United States Patent

Benhalima et al.

[11] Patent Number: 6,142,941
[45] Date of Patent: Nov. 7, 2000

[54] DEVICE FOR CARRYING OUT A TRANSOESOPHAGEAL ECHOCARDIOGRAPHY AND A CARDIOVERSION

[76] Inventors: Bouziane Benhalima; Zohra Lalaoui, both of 143, Avenue Jean Lolive, 93500 Pantin, France

[21] Appl. No.: 09/297,336

[22] PCT Filed: Oct. 31, 1997

[86] PCT No.: PCT/FR97/01958

§ 371 Date: Jun. 7, 1999

§ 102(e) Date: Jun. 7, 1999

[87] PCT Pub. No.: WO98/18519

PCT Pub. Date: May 7, 1998

[30] Foreign Application Priority Data

Oct. 31, 1996 [FR] France ................................. 96 13367

[51] Int. Cl.[7] .............................. A61B 8/12; A61N 29/00
[52] U.S. Cl. ........................... 600/439; 600/463; 607/119; 607/124
[58] Field of Search ..................... 600/380, 437, 600/439, 459, 471, 462–463; 607/124, 5, 119

[56] References Cited

U.S. PATENT DOCUMENTS

| | | | |
|---|---|---|---|
| 5,105,819 | 4/1992 | Wollschläger et al. | 600/463 |
| 5,178,149 | 1/1993 | Imburgia et al. . | |
| 5,191,885 | 3/1993 | Bilof et al. | 600/380 |
| 5,228,441 | 7/1993 | Lundquist | 600/380 |
| 5,299,578 | 4/1994 | Rotteveel et al. | 600/463 |
| 5,325,860 | 7/1994 | Seward et al. | 600/439 |
| 5,343,860 | 9/1994 | Metzger et al. | 600/380 |
| 5,417,713 | 5/1995 | Cohen | 607/4 |
| 5,749,833 | 5/1998 | Hakki et al. | 600/380 |

FOREIGN PATENT DOCUMENTS 0 104 287    4/1984   European Pat. Off. .
WO 90/13259 11/1990  WIPO .

*Primary Examiner*—Francis J. Jaworski
*Attorney, Agent, or Firm*—Young & Thompson

[57] ABSTRACT

The invention concerns a device for carrying out a transespohageal echocardiography and a cardioversion and includes a single endoscope (1) provided at its distal end with an ultrasonic sensor (3) and in the proximity of its distal end with at least one electrode (8) for generating electric shocks. The invention is usefull for the treatment of auricular fibrillation.

10 Claims, 2 Drawing Sheets

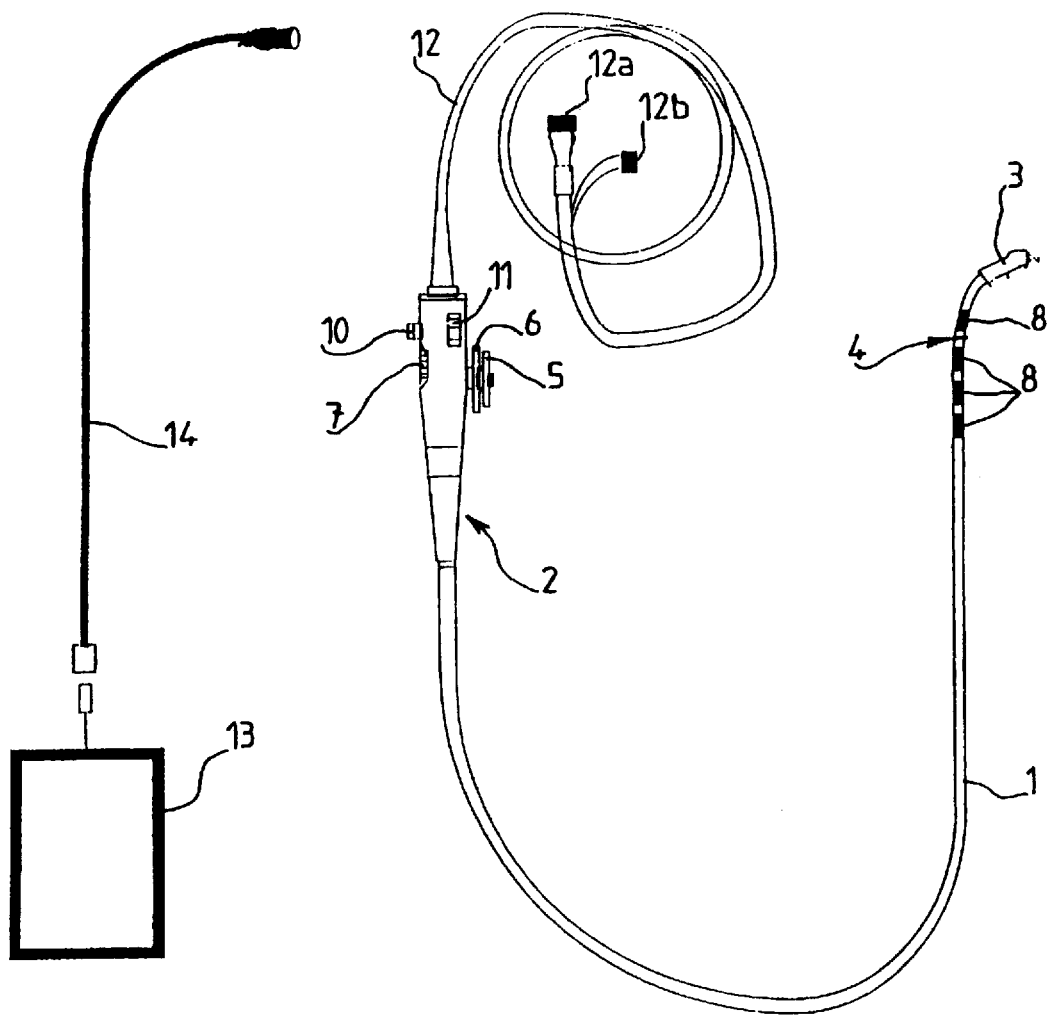

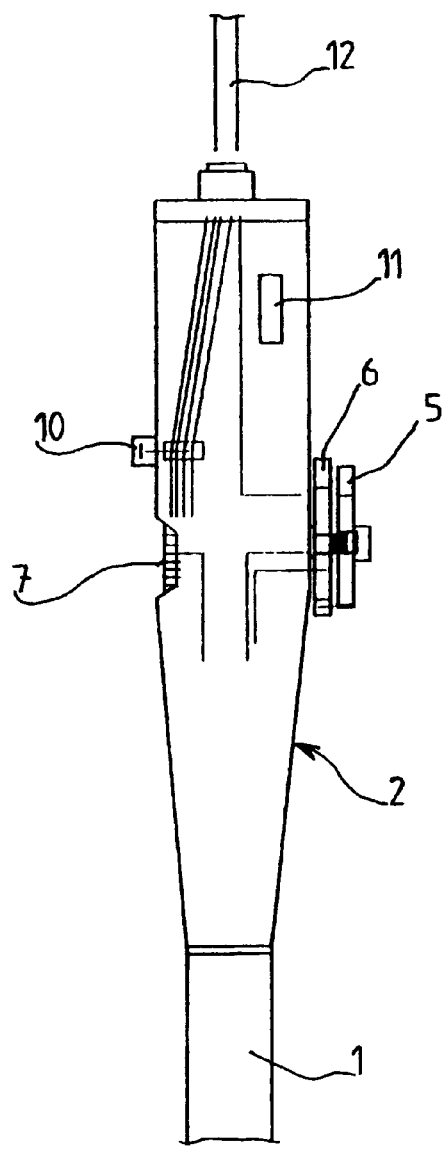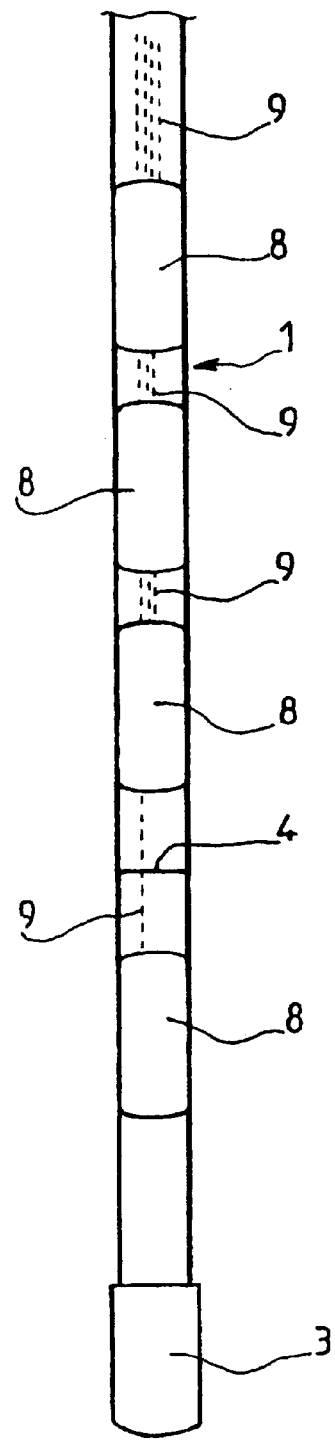

DEVICE FOR CARRYING OUT A TRANSOESOPHAGEAL ECHOCARDIOGRAPHY AND A CARDIOVERSION

BACKGROUND OF THE INVENTION

1. Field of the Invention

The present invention relates to a device for carrying out trans-esophageal echocardiography and a cardioversion, particularly for the treatment of arrhythmia.

2. Description of the Related Art

There will now be referred specifically to the arrhythmia which is the most frequent, which is auricular fibrillation, without thereby limiting the invention to this particular pathology. Auricular fibrillation is nowadays the arrhythmia most often encountered in a population more and more stressed and this the more as the population ages.

The risks connected with auricular fibrillation are numerous, particularly the risk of thromboembolic accident which can lead to cerebral vascular accidents responsible for very high morbidity and mortality, as well as a decrease of the cardiac flow due to loss of the auricular systole and to the change in systolic function of the left ventricle.

Thus, to prevent thromboembolic complications, to improve the left ventricular function and to recover the auricular systole, there is generally used a cardioversion to re-establish the sinusal rhythm in the patient by electric shock.

However, cardioversion can lead to cerebral vascular accidents or to peripheral embolisms, by detachment of all or a portion of the pre-existing thrombus at the level of the left auricle under the action of electric shock.

In the absence of reliable methods for the detection of thrombi, it was recommended to subject each patient to a treatment with anticoagulant for three weeks before the cardioversion and for four weeks after the return to normal sinusal rhythm, to dissolve any possible thrombi already existing. However, this treatment could lead to hemorrhaging, particularly in older subjects, to say nothing of possible complications connected to prolonged hospitalization.

Nowadays, it is possible to detect the presence of auricular thrombi by using trans-esophageal echocardiography, to visualize correctly the left auricle. A probe known for trans-esophageal echocardiography comprises generally an ultrasonic detector at the distal end of an endoscope. This latter method requires only a short anticoagulant regime for its use. When the result of trans-esophageal echocardiography reveals the absence of thrombi, one can proceed immediately to cardioversion.

Numerous methods of cardioversion are now known.

A first method consists in re-establishing the sinusal rhythm by pharmacological treatment by an oral or intravenous route. However, this method is of long duration and now is not always effective.

Another method consists in producing electric shocks internally or endocavitally. However, such a method of cardioversion is an invasive action and very difficult to use.

Still another method consists in producing electric shocks by esophagal route with an endoscope provided at its distal end with several electrodes. Although this operation does not require general anaesthetic, but only simple sedation, it can give rise to complications when it follows a preliminary trans-esophageal echocardiography. Thus, in practice, the operator sometimes encounters difficulties in reintroducing a new probe in the mouth of the patient through which it must pass, because there is a risk of rejection of the probe by the patent because the esophagal tissues are already irritated, to say nothing of the risks of injury or perforation of the esophagus by repeated introduction of endoscopes.

As a result, the cardioversion that is the most frequently used and preferred by doctors is cardioversion by external route in which two electrodes are simply applied to the thorax of the patient thereby to apply electrical discharges of the order of 300 to 360 J. This method is quite simple and easy to use for the doctor but it requires general anaesthetic for the patient.

SUMMARY OF THE INVENTION

The present invention therefore has for its object to eliminate the mentioned drawbacks and to provide a new device to carry out trans-esophageal echocardiography and a cardioversion which will be rapid and simple to use, effective for the treatment of arrhythmia and relatively well tolerated by the patient.

To this end, the invention has for its object a device for carrying out trans-esophageal echocardiography and a cardioversion, comprising an endoscope provided at its distal end with an ultrasonic detector for echocardiography, characterized in that the same endoscope is provided with at least one electrode adjacent its distal end to provide electric shocks for a cardioversion by esophagal route.

Thus, both echocardiography and cardioversion can be carried out during the same operation either simultaneously or successively, without requiring several introductions and withdrawals of probes through the esophagus. The risk of laceration of the esophagus and rejection of the probe by the patient is thus substantially reduced.

In a preferred embodiment, the distal portion of the endoscope which comprises the detector is articulated relative to the rest of the endoscope, controlled as to flexure and provided with at least one electrode. The fact of providing at least one electrode on the articulated distal portion of the endoscope permits bringing this electrode most closely to the auricular tissue and to ensure perfect contact between the remaining electrodes and the subjacent portion of the auricular tissue at the moment of cardioversion. Thus, the quantity of energy necessary for cardioversion can be optimized and reduced. In particular, there can be provided at least one electrode on the articulated distal portion of the endoscope between the articulated portion and the detector, and at least one other electrode on the flexible distal portion which is not articulated, of the endoscope, adjacent the articulated portion.

According to a particular characteristic, the end distal electrode is located about 4–5 cm from the distal end of the endoscope and about 1 cm from the articulated portion. There can be provided at least four electrodes extending over a distance of about 12 cm from the distal end of the endoscope.

According to another characteristic, the endoscope is provided at its proximal end with a handle incorporating the control members for the flexing of the articulated distal portion, for the rotation of a multi-plane ultrasonic detector, and for triggering electric shocks.

In a particular embodiment, the guide for actuating the articulated portion of the endoscope and the electrical connection wires of the electrodes, are coaxially disposed in the endoscopic tube. Each electrode can be connected independently to the handle of the endoscope.

BRIEF DESCRIPTION OF THE DRAWINGS

The invention will be better understood, and other objects, details, advantages and characteristics of the latter will become apparent more clearly in the course of the explanation which follows, of a particular embodiment of the invention that at the moment is preferred, given solely by way of illustration and not limitation, with reference to the accompanying schematic drawings, in which:

FIG. 1 is a schematic plan view of the device of the invention.

FIG. 2 is a fragmentary enlarged view of the distal portion of the endoscope of FIG. 1.

FIG. 3 is a fragmentary enlarged view of the control handle of the device of FIG. 1.

FIG. 4 is a schematic plan view of the device for connection of the thoracic electrode for cardioversion by the esophagal route.

DESCRIPTION OF THE PREFERRED EMBODIMENTS

According to the embodiment shown in the drawings, the device of the invention comprises a single flexible tubular endoscope 1 of a structure known per se, and connected at its proximal end to a control handle 2 and comprising at its distal end an ultrasonic transducer assembly 3.

The distal portion of the endoscope 1 which comprises the multi-plane detector 3 is articulated at 4 relative to the rest of the endoscope. This articulated distal portion is manipulated by bending by means of a control guide (not shown) coaxially disposed in the endoscopic tube 1, by two dials 5 and 6 provided on the handle 2. One of the dials permits vertical displacement of the articulated distal portion and the other dial permits horizontal displacement of this latter. One of the dials, for example the large dial 6, permits controlling movements of deflection of the articulated distal portion, in a plane parallel to its axis upwardly and downwardly, with an angle of up to 90°, the other dial in lateral deflections in a plane perpendicular to the first. These movements are possible thanks to a system known per se, which is provided with a cable sliding on a pulley and fixed on opposite sides at the level of the articulated portion, upwardly and downwardly for one and on its lateral sides for the other. Moreover, each dial is provided with an independent brake actuable by pushing on the selected dial. The brake will be deactivated by pulling on the suitable dial. Thus, by maneuvering the dials 5 and 6, the distal portion with the detector 3 and the electrode 8 can be positioned exactly in the esophagus and the brakes permit the articulated distal portion to keep its position. This can be changed only after having pulled on the dials. Thus, by manipulating the dials 5 and 6, the detector 3 can be positioned exactly in the esophagus.

At 7 is shown another manual dial which permits controlling the rotation of the cross-sectional plane of the ultrasonic detector 3 which is annularly mechanically directed.

There is seen in FIGS. 1 and 2, four annular electrodes 8 of which one is positioned on the same articulated distal portion as the detector 3 and the other three are positioned on the non-articulated portion of the endoscope adjacent the articulated portion 4. It will be seen in FIG. 2 that each electrode 8 is connected by a wire 9 independently to the control handle 2.

By way of example, these four electrodes are arranged along the length by about 12 cm from the distal end of the endoscope, each electrode having a length of about 2 cm. The end distal electrode can be disposed at a distance of about 4.5 cm from the distal end of the endoscope in its articulated portion. The distance between the end distal electrode and the following electrode on the non-articulated portion can be about 2 cm, whilst the remaining electrodes are spaced only by 1 cm.

It will be better seen in FIGS. 1 and 3 that the control handle 2 comprises moreover a button 10 for energy charging and triggering the electric shock. By a first short pressure, the condenser of the defibrillator (not shown) will be charged and by a second following pressure on the same button 10, electric charge will be discharged through the electrodes 8 for re-establishing the sinusoidal rhythm.

The control handle 2 moreover comprises a numerical display screen 11 to indicate the number of Joules selected for the electric charge to be triggered as well as a sonic warning to indicate the end of charging. The control handle 2 is connected in its turn by a cable 12, on the one hand to an electrocardiographic apparatus (not shown) by a connector 12a, and, on the other hand, to the defibrillation apparatus by a connector 12b. The cable 12 thus divides at its distal end for its connection respectively to the electrocardiographic apparatus and the defibrillation apparatus.

Finally, there will be seen in FIG. 4 an external self-adhesive electrode 13 for single use which is adapted to be applied to the sternum of the patient to constitute the cathode of the cardioversion apparatus. The external electrode 13 is connected by a standard cable 14 to the defibrillator apparatus.

Of course, the number of electrodes can vary as a function of the applications envisaged and the operator can actuate simultaneously or successively the electrocardiograph and the defibrillator.

The endoscope 1 is provided with several electrodes 8 to increase the energy transfer surface at the moment of defibrillation. The electrodes are arranged in a circular manner.

There will now be briefly described the operation of the device of the invention.

The endoscopic probe is first introduced into the esophagus of the patient by passing through its mouth through block for the teeth. The endoscope is positioned in the esophagus such that the ultrasonic detector 3 permits visualizing the valves and auricles of the heart at a distance of 30–40 cm from the dental arch so as to eliminate the presence of a thrombus, this position being maintained by actuating the brake of the dials 5 and 6. Thus, the articulated portion permits the first electrode to approach closely the myocardial wall and that thanks to bending which is assured by the large dial. After positioning the articulated distal portion, the operator is able, thanks to the button 10, to control the carrying out of cardioversion. He then selects a suitable charge of electrical energy and a first actuation of the button 10 permits this charge to take effect under control of the indicator 11 provided with a sonic blip which indicates the end of the selected charge. After the sonic blip, the operator can carry out the movement of triggering the discharge. Thanks to these easy working conditions, the cardiologic operator can actuate himself the device and carry out this operation several times. Moreover, the self-sticking external electrode 13 is positioned on the sternum to permit defibrillation in the course of the same operation.

It will moreover be seen that the user of this device can shorten the time the patient is involved and can improve his comfort.

The use of the device requires but a short anticoagulant regime and light sedation.

Although the invention has been described in connection with a particular embodiment, it is of course evident that it is not thereby limited and that it comprises all the technical equivalents of the described means as well as their combination if the latter enter into the scope of the invention.

It should be remembered that the device according to the invention ensures diagnosis by means of electrocardiography, namely the electric sonic detector, and therapy by delivery of a previously adjusted electrical discharge (that is to say by cardioversion and hence restoration of the sinusal rhythm). The arrangement of an electrode on the articulated portion, thus near the ultrasonic detector, gives to the operator the possibility of visualizing exactly the position in which he should practice cardioversion. This also gives the possibility of being guided, which gives technically good control. This arrangement permits moreover studying the behavior of the left auricle (degree of appearance of contrast, formation of thrombi) at the time of cardioversion and hence controlling the administration of anticoagulant.

This is a major advantage of the invention, because within the scope of restoration of sinusal rhythm by cardioversion, according to the invention, it is very important to ensure close approach of the electrode to the heart wall. Thus, the closer the electrode is to the heart wall, the better is the efficiency. The presence of an electrode in the distal articulated portion thus permits better contact, even a sandwich arrangement.

Another major advantage of the invention resides in the fact that the button 10 located on the control handle of the device ensures the cardiological operator complete independence from his assistants. Thus, the device permits the operator to carry out all the operations alone, whenever he deems necessary, instead of requiring assistants, especially in emergency situations or in the situation in which the first electric shock has not restored sinusal rhythm. It is possible to repeat this operation up to three consecutive times.

What is claimed is:

1. Device to carry out trans-esophageal echocardiography and cardioversion, comprising:
   an endoscopic tube (1) having a proximal end and a distal end;
   an ultrasonic transducer (3) provided at said distal end and structured to allow connection to an electrocardiographic apparatus;
   an articulation (4) provided in said endoscopic tube, and defining, on one side of said articulation, a proximal portion between said articulation and said proximal end, and on another side of said articulation, a distal portion between said articulation and said distal end;
   control guides coaxially disposed in said endoscopic tube and connecting said distal portion to a control handle (2) provided at said proximal end, for bending said distal portion with respect to said proximal portion;
   at least one first electrode (8) provided on said distal portion;
   a plurality of second electrodes (8) provided on said proximal portion;
   wherein the control guides allow the distal portion to be bent so that the at least one first electrode and at least one of the plurality of second electrodes may be moved toward one another to sandwich intervening tissue;
   each of said first and second electrodes being connected by a cable (9) in said endoscopic tube, each cable being structured to allow connection to a defibrillator to produce electric shocks for a cardioversion.

2. Device according to claim 1, wherein one of said at least one first electrode is located at about 4–5 cm from the distal end of the endoscopic tube and at about 1 cm from the articulation (4).

3. Device according to claim 1, wherein the first and second electrodes number at least four and extend over a distance of about 12 cm from the distal end of the endoscopic tube.

4. Device according to claim 1, wherein the articulated distal portion may be flexed by actuation of the control guides in a first plane parallel to its axis upwardly and downwardly, through an angle up to 90°, and in a second plane perpendicular to the first plane for lateral deflections.

5. Device according to claim 1, wherein the endoscopic tube (1) is provided at the proximal end with a handle (2) incorporating control members (5 and 6) for bending of the articulated distal portion.

6. Device according to claim 1, wherein the endoscopic tube (1) is provided at its proximal end with a handle (2) incorporating a control member (7) which allows rotation of the ultrasonic transducer (3) disposed on the distal portion of the endoscope, the ultrasonic transducer being a multi-plane ultrasonic transducer.

7. Device according to claim 1, wherein the endoscopic tube (1) is provided at the proximal end with a handle (2) comprising a means (10) for charging electrical energy adapted to produce the electric shocks and for triggering said shocks.

8. Device according to claim 1, wherein each electrode (8) is connected independently to the control handle (2) of the endoscopic tube.

9. Device to carry out trans-esophageal echocardiography and cardioversion, comprising:
   an endoscopic tube (1) having a proximal end and a distal end;
   an ultrasonic transducer (3) provided at said distal end and structured to allow connection to an electrocardiographic apparatus;
   an articulation (4) provided in said endoscopic tube, and defining, on one side of said articulation, a proximal portion between said articulation and said proximal end, and on another side of said articulation, a distal portion between said articulation and said distal end;
   control guides coaxially disposed in said endoscopic tube and connecting said distal portion to a control handle (2) provided at said proximal end, for bending said distal portion with respect to said proximal portion;
   at least one first electrode (8) provided on said distal portion;
   a plurality of second electrodes (8) provided on said proximal portion;
   wherein the control guides allow the distal portion to be bent so that the at least one first electrode and at least one of the plurality of second electrodes may be moved toward one another to sandwich intervening tissue;
   each of said first and second electrodes being connected by a cable (9) in said endoscopic tube, each cable being structured to allow connection to a defibrillator to produce electric shocks for a cardioversion;
   wherein each of the first and second electrodes (8) is spaced from an adjacent said electrode by a distance of 1 to 2 cm, and wherein said ultrasonic transducer (3) is spaced from a closest one of said at least one first electrode by a distance of 4 to 5 cm.

10. Device according to claim 9, wherein the control guides of the articulated portion of the endoscopic tube (1) and the cable (9) for electrical connection with the first and second electrodes (8) are coaxially disposed in the endoscopic tube.

* * * * *